(12) United States Patent
Shin et al.

(10) Patent No.: US 9,233,128 B2
(45) Date of Patent: Jan. 12, 2016

(54) USE OF CRYPTOTANSHINONE

(71) Applicant: Catholic University Industry Academic Cooperation Foundation, Seoul (KR)

(72) Inventors: Jin Hee Shin, Seoul (KR); Kyung Soo Kim, Seoul (KR); Il Kyu Lee, Seoul (KR)

(73) Assignee: CATHOLIC UNIVERSITY INDUSTRY ACADEMIC COOPERATION FOUNDATION (KR)

( * ) Notice: Subject to any disclaimer, the term of this patent is extended or adjusted under 35 U.S.C. 154(b) by 13 days.

(21) Appl. No.: 14/073,561

(22) Filed: Nov. 6, 2013

(65) Prior Publication Data

US 2014/0134138 A1 May 15, 2014

Related U.S. Application Data

(63) Continuation of application No. 13/877,214, filed as application No. PCT/KR2011/007324 on Oct. 4, 2011, now abandoned.

(30) Foreign Application Priority Data

Oct. 1, 2010 (KR) .................. 10-2010-0096039

(51) Int. Cl.
 *A61K 35/28* (2015.01)
 *A61K 31/122* (2006.01)
 *A61K 31/343* (2006.01)
 *C12N 5/077* (2010.01)

(52) U.S. Cl.
 CPC ............... *A61K 35/28* (2013.01); *A61K 31/343* (2013.01); *C12N 5/0654* (2013.01); *C12N 2501/999* (2013.01); *C12N 2506/1384* (2013.01)

(58) Field of Classification Search
 None
 See application file for complete search history.

(56) References Cited

U.S. PATENT DOCUMENTS

2011/0081323 A1* 4/2011 Kleinsek et al. ............. 424/93.7
2012/0201791 A1 8/2012 Yoo

OTHER PUBLICATIONS

Wong, R.W.K., and Rabie, A.B.M. "Effect of Salvia miltiorrhiza extract on bone formation", Journal of Biomedical Materials Research Part A 2007, vol. 85, pp. 506-512.*
Kim, H.J., and Kim, S.H., "Tanshinone IIA enhances BMP-2-stimulated commitment of C2C12 cells into osteoblasts via p38 activation", Amino Acids 2010, vol. 39, pp. 1217-1226.*
Dai, H., Wang, M., Li, X., Wang, L., Li, Y., and Xue, M., "Structural elucidation of in vitro and in vivo metabolites of cryptotanshinone by HPLC-DAD-ESI-MS", Journal of Pharmaceutical and Biomedical Analysis 2008, vol. 48, pp. 885-896.*
Lee et al. (2005) Archives of Pharmacal Research 28(8):909-913 "Inhibition of Osteoclast Differentiation by Tanshinones from the Root of *Salvia miltiorrhiza* Bunge".
Tamer and Reis (2009) Journal of Tissue Engineering and Regenerative Medicine 3:327-337 "Progenitor and stem cells for bone cartilage regeneration".

* cited by examiner

*Primary Examiner* — Renee Claytor
*Assistant Examiner* — Michelle F Paguio Frising
(74) *Attorney, Agent, or Firm* — Swanson & Bratschun, L.L.C.

(57) ABSTRACT

Provided are a composition for stimulating differentiation of MSCs into osteoblasts, which includes cryptotanshinone, and an osteogenesis stimulator including cryptotanshinone and MSCs. When the cryptotanshinone is treated to the MSCs, the differentiation into osteoblasts is stimulated, and thus osteogenesis of a patient may be stimulated by directly transplanting the differentiation-induced MSCs to the patient. Accordingly, the composition or osteogenesis stimulator may be used to treat patients having disability requiring stimulation of osteogenesis such as osteoporosis, bone fracture, bone grafting including alveolar bone grafting for implant placement, or other bone defects.

6 Claims, 2 Drawing Sheets

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Runx 2 forward primer

<400> SEQUENCE: 1
ccgcacgaca accgcaccat                                                     20

<210> SEQ ID NO 2
<211> LENGTH: 20
<212> TYPE: DNA
<213> ORGANISM: Artificial Sequence
<220> FEATURE:
<223> OTHER INFORMATION: runx2 reverse primer

<400> SEQUENCE: 2
cgctccggcc cacaaatctc                                                     20

<210> SEQ ID NO 3
<211> LENGTH: 20
<212> TYPE: DNA
<213> ORGANISM: Artificial Sequence
<220> FEATURE:
<223> OTHER INFORMATION: osteocalcin forward primer

<400> SEQUENCE: 3
atgagagccc tcacactcct                                                     20

<210> SEQ ID NO 4
<211> LENGTH: 20
<212> TYPE: DNA
<213> ORGANISM: Artificial Sequence
```

```
<220> FEATURE:
<223> OTHER INFORMATION: osteocalcin reverse primer

<400> SEQUENCE: 4
caagggaaag aggaaagaag                                               20

<210> SEQ ID NO 5
<211> LENGTH: 20
<212> TYPE: DNA
<213> ORGANISM: Artificial Sequence
<220> FEATURE:
<223> OTHER INFORMATION: collagen type I forward primer

<400> SEQUENCE: 5
ggacacaatg gattgcaagg                                               20

<210> SEQ ID NO 6
<211> LENGTH: 20
<212> TYPE: DNA
<213> ORGANISM: Artificial Sequence
<220> FEATURE:
<223> OTHER INFORMATION: collagen type I reverse primer

<400> SEQUENCE: 6
taaccactgc tccactctgg                                               20

<210> SEQ ID NO 7
<211> LENGTH: 23
<212> TYPE: DNA
<213> ORGANISM: Artificial Sequence
<220> FEATURE:
<223> OTHER INFORMATION: osteonectin forward primer

<400> SEQUENCE: 7
tcttccctgr acactggcag ttc                                           23

<210> SEQ ID NO 8
<211> LENGTH: 20
<212> TYPE: DNA
<213> ORGANISM: Artificial Sequence
<220> FEATURE:
<223> OTHER INFORMATION: osteonectin reverse primer

<400> SEQUENCE: 8
agctcggtgt gggagaggta                                               20

<210> SEQ ID NO 9
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 9
ccgcatcttc ttttgcgtcg c                                             21

<210> SEQ ID NO 10
<211> LENGTH: 25
<212> TYPE: DNA
<213> ORGANISM: Artificial Sequence
<220> FEATURE:
<223> OTHER INFORMATION: GAPDH reverse primer

<400> SEQUENCE: 10
gcaactgtga ggaggggaga ttcag                                         25
```

USE OF CRYPTOTANSHINONE

RELATED APPLICATIONS

This application is a continuation of U.S. patent application Ser. No. 13/877,214, filed on Apr. 1, 2013, entitled "Novel Use of Cryptotanshinone", which application is a 35 U.S.C. §371 national phase application of PCT/KR2011/007324 (WO 2012/044139), filed on Oct. 4, 2011, entitled "Novel Use of Cryptotanshinone", which application claims the benefit of Korean Application Serial No. 10-2010-0096039, filed Oct. 1, 2010, which are incorporated herein by reference in their entirety.

TECHNICAL FIELD

The present invention relates to a novel use of cryptotanshinone.

Incorporated by reference herein in its entirety is the Sequence Listing entitled "338.75-PCT-US-C_ST25. txt," created Jan. 22, 2014, size 3 kilobytes,.

BACKGROUND

As a technique for treating tissues and organs damaged by various kinds of diseases, a method of injecting self-renewable and differentiable cells to the tissues and organs to be renewed is receiving attention. A representative example of the cells may be mesenchymal stem cells (MSCs).

The MSCs are multipotent stem cells, which can be differentiated into various kinds of cells. Since the MSCs may be differentiated into various cells and tissues constituting a human body such as osteoblasts, chondrocytes, adipocytes, neuronal cells, epithelial cells, muscles, etc., they are in the limelight as the most critical cells in terms of practice of regenerative medicine. However, to obtain a satisfactory therapeutic effect, it is important the MSCs injected to a tissue are suitably differentiated, and engrafted to a corresponding tissue.

Adipocytes originate from mesoderm-originating stem cells, which can be differentiated into osteoblasts, as well as the adipocytes. According to various studies, it was shown that there is a contrary relationship between differentiations of bone marrow-derived stem cells into adipocytes and osteoblasts (Dorheim M A, et al., J Cell Physiol 1993; 154:317-28.; Beresford J N, et al., J Cell Sci 1992; 102:341-51.). That is, as the differentiation into adipocytes is inhibited, osteogenesis can be increased. It was shown that many transcription factors and intracellular and extracellular signal transduction pathways are closely associated and regulated in the process of differentiating stem cells into adipocytes and osteoblasts. Among the transcription factors, a peroxisome proliferator-activated receptor γ (PPARγ) serves to increase the differentiation into adipocytes, but decrease the differentiation into osteoblasts (Schwartz A V, et al., J Clin Endocrinol Metab 2006; 91:3349-54.; Gimble J M, et al., Mol Pharmacol 1996; 50:1087-94.).

Meanwhile, cryptotanshinone, which is a fat-soluble diterpene-based compound extracted from a dried root of *Salvia militorrhiza* Bunge, was known to have a pharmacological action of declining an appetite. In an animal test with respect to obese rats, the decline in an appetite and 30% loss of a weight were observed after administration of the cryptotanshinone. However, there were no reports that the cryptotanshinone stimulates the differentiation of stem cells into osteoblasts.

SUMMARY OF THE EMBODIMENTS

The present invention is directed to providing a novel use of cryptotanshinone.

The inventors surprisingly found that cryptotanshinone can stimulate differentiation of MSCs into osteoblasts in the study for cryptotanshinone inhibiting differentiation of adipose tissue-derived MSCs into adipocytes.

In the following Examples, according to confirmation of mineral deposition of osteoblasts through alkaline phosphatase (ALP) staining and calcium deposition occurring in osteogenesis through von Kossa staining, it is confirmed that stem cells are changed into osteoblasts in a cryptotanshinone-treated medium. It can be also confirmed that genes to be expressed in the differentiation into osteoblasts such as Runx2, collagen type I, osteonectin, and osteocalcin are expressed. In addition, it can be confirmed that, in the cryptotanshinone-treated medium, differentiation of stem cells into osteoclasts is inhibited.

Accordingly, in one aspect, the present invention provides a composition including cryptotanshinone, which serves to stimulate differentiation of MSCs into osteoblasts. The composition is useful for a therapy method for transplanting osteoblasts to treat diseases requiring stimulation of osteogenesis, such as osteoporosis, bone fracture, bone grafting including alveolar bone grafting for implant placement, or other bone defects.

A method of stimulating differentiation of MSCs into osteoblasts using the composition is not particularly limited. For example, during culture of the MSCs to be transplanted to a patient requiring osteogenesis, the composition may be additionally added to the culture medium, and thus may stimulate the differentiation of the stem cells into osteoblasts. Alternatively, the composition may be treated together when the MSCs are transplanted.

A kind of the MSCs capable of stimulating the differentiation into osteoblasts by the composition is not particularly limited.

In one embodiment, the MSCs may be obtained from tissues, bone marrow, cord blood, or blood. In one embodiment, the MSCs may be obtained from an adipose tissue.

A concentration of the cryptotanshinone capable of stimulating the differentiation of MSCs into osteoblasts may be, but is not particularly limited to, 1 to 50 μM.

Meanwhile, the composition may include a medium generally used in the culture of the MSCs. As such a medium, but not limited to, for example, a minimum essential medium alpha (MEM-alpha), a mesenchymal stem cell growth medium (MSCGM), or a Dulbecco's modified Eagle's medium (DMEM) may be included. In addition, a medium known in the related art to stimulate the differentiation into osteoblasts, for example, an osteoblast differentiation-inducing medium such as MEMα including Dexamethasone, glycerol phosphate, and L-ascorbic acid 2-phosphate may be used.

In another aspect, the present invention provides an osteogenesis stimulator including cryptotanshinone and MSCs.

As described above, when the cryptotanshinone is treated to the MSCs, differentiation into osteoblasts is stimulated. Thus, the differentiation-induced MSCs may be directly transplanted to a patient, and osteogenesis of the patient may be stimulated.

In one embodiment, the osteogenesis stimulator may be used in grafting to a patient having disability, who requires stimulation of osteogenesis, such as osteoporosis, bone fracture, bone grafting including alveolar bone grafting for implant placement, or other bone defects.

In the specification, any one of the MSCs may be used without limitation to its origin.

In one embodiment, the MSCs may be obtained from tissues, bone marrow, cord blood, or blood. In one embodiment, the MSCs may be obtained from adipose tissues.

An animal, which is a target for collecting tissues, bone marrow, cord blood, or blood, may be a mammal. When the animal is a human, the tissues, bone marrow, cord blood, or blood may be derived from a patient him/herself or another human, to whom osteoblast differentiation-induced MSCs by the composition of the present invention will be administrated as a cell therapy product.

In the osteogenesis stimulator including the cryptotanshinone and the MSCs according to the present invention, the MSCs may be in a state of inducing the differentiation into osteoblasts by treatment of the cryptotanshinone, but in some cases, MSCs which are not treated with cryptotanshinone may be used for simultaneous transplantation with the cryptotanshinone. In addition, when the differentiation of the MSCs into osteoblasts by the cryptotanshinone is induced to a certain extent, the osteogenesis stimulator may include osteoblasts whose differentiation is induced by the cryptotanshinone, not the cryptotanshinone.

In another embodiment, the osteogenesis stimulator may be administrated by being contained in a carrier. The carrier may be any one known in the related art, which is used for transplantation of stem cells or bone grafting. For example, in the case of a patient requiring bone grafting such as alveolar bone grafting for implant placement, grafting of bone prosthesis may be generally performed. Here, the osteogenesis stimulator may be grafted by being contained in the bone prosthesis. In this case, a gel-type biocompatible polymer may help the induction of the differentiation of transplanted MSCs into osteoblasts through continuous supply of cryptotanshinone and engraftment. Likewise, in the case of a bone-fractured patient, when the osteogenesis stimulator is grafted using a biocompatible scaffold including a chitosan or hyaluronic acid as a carrier, the induction of the differentiation of stem cells into osteoblasts by cryptotanshinone may be continuously stimulated.

In one embodiment, the cryptotanshinone may be included at a concentration of 1 to 50 µM.

In addition, an effective amount of the MSCs may be $1 \times 10^4$ to $1 \times 10^6$ cells/kg. However, a dose of the MSCs may be suitably increased or decreased according to weights, ages, genders, or degrees of injury of patients. A medicine according to the present invention may be applied to a human body by parenteral or topical administration. To this end, an effective ingredient is suspended or dissolved in a pharmaceutically available carrier according to a conventional method, and here, a water-soluble carrier may be used.

According to the present invention, when cryptotanshinone is treated to MSCs, differentiation into osteoblasts is stimulated, and therefore, osteogenesis of a patient may be stimulated by directly transplanting the differentiation-induced MSCs. Accordingly, a composition or osteogenesis stimulator of the present invention can be used to treat a patient having disability requiring stimulation of the osteogenesis, such as osteoporosis, bone fracture, bone grafting including alveolar bone grafting for implant placement, or other bone defects.

MODE FOR INVENTION

Figure 1:
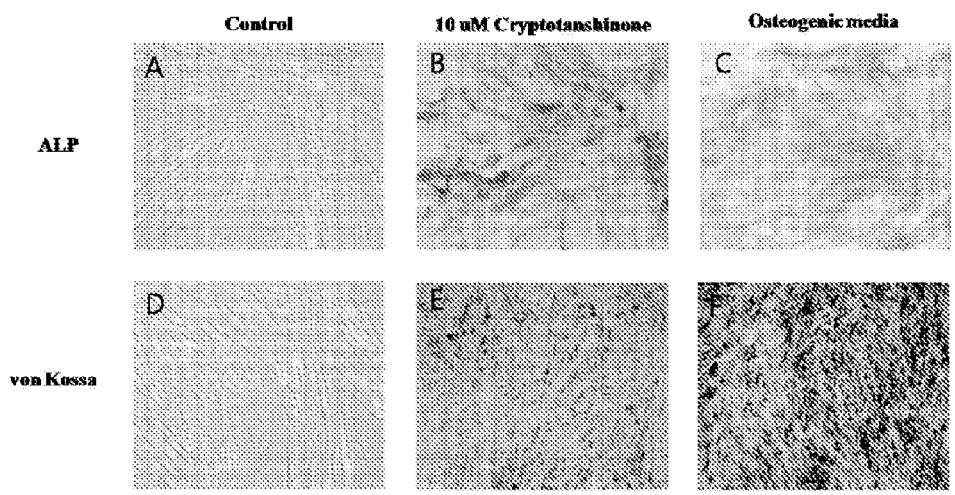
FIG. 1 shows results of ALP and von Kossa staining to confirm whether an adipose tissue-derived stem cell is or is not differentiated into osteoblasts by treatment of cryptotanshinone.

The advantages and features of the present invention and the method of revealing them will be explicit from the following examples described in detail, However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example 1

Isolation and Culture of Stem Cell

This research was conducted using an adipose tissue collected from a human body after receiving an approval from Institutional Review Board of Catholic University and a written consent according to Bioethics and Safety Act and Helsinki Declaration from patients.

Isolation of adipose tissue-derived stem cells (hADSCs) was conducted by a method suggested by Im G. I. et al. (Osteoarthritis Cartilage 2005; 13:845-53.). From a surgical specimen obtained from liposuction of 25-year female without a specific past medical history or drug history, an adipose tissue was obtained, and washed with phosphate buffered saline (PBS, Gibco BRL) including 1% antibiotic and antimycotic (10× antibiotic & antimycotic, Gibco BRL, Grand island, N.Y., USA). The tissue was cut into small pieces with a mess, treated with 0.06% collagenase type I (Invitrogen Corporation, Carlsbad, Calif., USA) and shake-cultured at 37° C. in a 5% $CO_2$ incubator (Forma Scientific Inc, Marietta, Ohio) for 4 hours. The cultured product was centrifuged (Large Capacity table top Centrifuge, Hanil Science) to obtain a precipitate, and then the precipitate was suspended in a minimum essential medium (MEM, Gibco BRL) containing 10% fetal bovine serums (Hyclone, Logan, Utah) and 1% penicillin-Streptomycin (P/S, Gibco BRL). Subsequently, the tissues were filtered with a 40 µm cell strainer (BD Bioscience, Two Oak Park, Bedford, Mass.), and a solution obtained through the filter was incubated. Afterward, morphological characteristics of the solution were examined under an inverted microscope every day, and a culture medium was changed every other day. When the medium was changed, cells not attached to a culture plate were removed, and only cells attached thereto were incubated until approaching a saturated state. The saturated cells were isolated using trypsin-EDTA (Gibco BRL), and subcultured three times.

Example 2

Confirmation of Induction of Differentiation of Adipose Tissue-derived Stem Cells into Osteoblasts by Cryptotanshinone 1) Induction of Differentiation into Osteoblasts The hADSCs subcultured at passage 3 were dispensed in a 12-well plate at 1×10 cells/well, a general medium (MEMα), a osteoblast differentiation-inducing medium (MEMα including 0.1 μm Dexamethasone, 10 μm glycerol phosphate, and 50 μm L-ascorbic acid 2-phosphate), or a medium treated with 10 μM cryptotanshinone was treated to the cells, and the medium was changed every third day. The cryptotanshinone was a solid having a standard solid content of 99.7%, provided from Yungjin Pharm.

2) Confirmation of Osteoblast Differentiation

To confirm the differentiation of stem cells into osteoblasts, first, ALP staining and von Kossa staining were performed. The ALP staining was used to confirm mineral deposition of the osteoblasts by forming a blue material, and the von Kossa staining was used to confirm calcium deposition occurring in osteogenesis, resulting in confirming the osteogenesis.

For ALP staining, each treatment group was washed with sterilized deionized (DI) water three times at 7, 14, 21, and 28 days after the treatment day, fixed with a citrate-acetone-formaldehyde (Sigma) fixing agent, and washed again with sterilized DI water three times. The treatment group was stained with an alkaline-dye mix (nitrite, FRV-alkaline, naphthol AS-BI alkaline solution, Sigma) at room temperature for 15 minutes with blocking of light, and washed with sterilized DI water three times. The treatment group was stained with hematoxylin, washed with sterilized DI water, three times, and examined under an inverted microscope.

For von Kossa staining, each treatment group was washed with sterilized DI water three times at 7, 14, 21, and 28 days after the treatment day, fixed with 4% paraformaldehyde at room temperature for 15 minutes, and washed again with DI water three times. The treatment group was stained with a 1% silver nitrate aqueous solution for 30 minutes with blocking of light, washed with DI water three times, and exposed to a UV ray for 1 hour. The treatment group was stained with 0.1% Eosin (Sigma), and examined under the inverted microscope.

As a result, as shown in FIG. 1, it was confirmed that the differentiation of the stem cells into the osteoblasts started from the $7^{th}$ day and increased up to the $28^{th}$ day in the osteoblast differentiation medium, there was no change in the general medium, and the differentiation into the osteoblasts occurred at the $28^{th}$ day in the medium treated with 10 μM cryptotanshinone (refer to FIGS. 1A to 1F).

Subsequently, using a reverse transcription polymerase chain reaction (RT-PCR), genes, which were expressed when osteoblast differentiation was induced, were confirmed.

Each treatment group was washed with PBS (Gibco BRL) at 7, 14, 21, and 28 days after the treatment day, cells were harvested using a cell scraper (Sarsted, Inc, Newton, N.C.), RNAs were isolated therefrom using a QIAGEN RNA extraction kit (QIAGEN, GmbH, Germany), and then the RT-PCR was performed using the following conditions.

| Name | Primer | | | Annealing |
|---|---|---|---|---|
| osteogenic | Runx2 | forward | 5'-CCGCACGACAACCGCACCAT-3' (SEQ ID NO: 1) | 58 |
| | | reverse | 5'-CGCTCCGGCCCACAAATCTC-3' (SEQ ID NO: 2) | |
| | Osteocalcin | forward | 5'-ATGAGAGCCCTCACACTCCT-3' (SEQ ID NO: 3) | 51 |
| | | reverse | 5'-CAAGGGGAAGAGGAAAGAAG-3' (SEQ ID NO: 4) | |
| | Collagen type I | forward | 5'-GGACACAATGGATTGCAAGG-3' (SEQ ID NO: 5) | 58 |
| | | reverse | 5'-TAACCACTGCTCCACTCTGG-3' (SEQ ID NO: 6) | |
| | Osteonectin | forward | 5'-TCTTCCCTGTACACTGGCAGTTC-3' (SEQ ID NO: 7) | 55 |
| | | reverse | 5'-AGCTCGGTGTGGGAGAGGTA-3' (SEQ ID NO: 8) | |
| control | GAPDH | forward | 5'-CCGCATCTTCTTTTGCGTCGC-3' (SEQ ID NO: 9) | 52 |
| | | reverse | 5'-GCAACTGTGAGGAGGGGAGATTCAG-3' (SEQ ID NO: 10) | |

PCR Conditions:
1. Incubation for 2 minutes at 94° C.
2. Denaturation for 45 seconds at 94° C.
3. Annealing at 51 to 60° C.
4. Polymerization 32 cycles for 60 seconds at 72° C.
5. Extension for 5 minutes at 72° C.

A product obtained through the RT-PCR was analyzed twice using 2% agarose gel electrophoresis.

Figure 2:
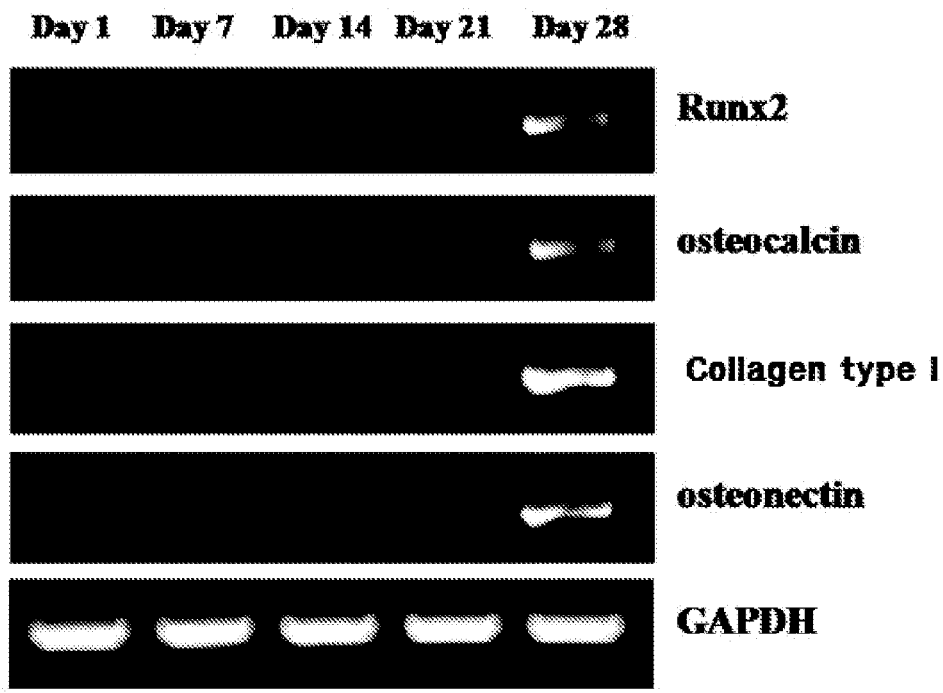
FIG. 2 shows RT-PCR results for confirming expression of a marker expressed in induction of osteoblast differentiation to confirm the differentiation of adipose tissue-derived stem cells into osteoblasts by treatment of cryptotanshinone.

As a result, as shown in FIG. 2, expressions of specific genetic factors such as Runx2, collagen type I, osteonectin, and osteocalcin expressed in the osteoblast differentiation were observed in the medium treated with 10 μM cryptotanshinone from the $28^{th}$ day.

Example 3

Confirmation of Inhibition of Differentiation of Adipose Tissue-Derived Stem Cells into Osteoclasts by Cryptotanshinone 1) Induction of Differentiation into Osteoclasts The hADSCs subcultured at passage 3 were dispensed and incubated in culture plates each containing 100 nM Dexamethasone (Sigma-Aldrich, St. Louis, Mo.), an osteoclast differentiation medium (DMEM including 4 mM L-glutamine, 1.0 mM sodium pyruvate, 10% fetal bovine serum, 1% P/S, 20 ng/mL M-CSF, and 100 ng/mL RANKL), a medium prepared by adding 10 μM cryptotanshinone to 100 nM dexamethasone, and a medium prepared by adding 10 μM cryptotanshinone to the osteoclast differentiation medium for 7 days, and the mediums were changed every third day.

2) Confirmation of Differentiation into Osteoclasts

A tartrate resistant acid phosphatase (TRAP) is a material secreted from osteoclasts associated with active bone resorption. As the material is identified, the formation of osteoclasts may be observed. For this reason, to confirm the differentiation into osteoclasts, TRAP activity was measured.

First, after an osteoclast differentiation medium, a medium prepared by adding 10 μM cryptotanshinone to the osteoclast differentiation medium, and a general medium were treated to the cells, the cells were washed with PBS three times at 7 days after the treatment day, fixed with 4% paraformaldehyde, and stained using a TRAP assay kit (Takara Bio Inc., Shiga, Japan) to examine the cells under the inverted microscope.

Figure 3:
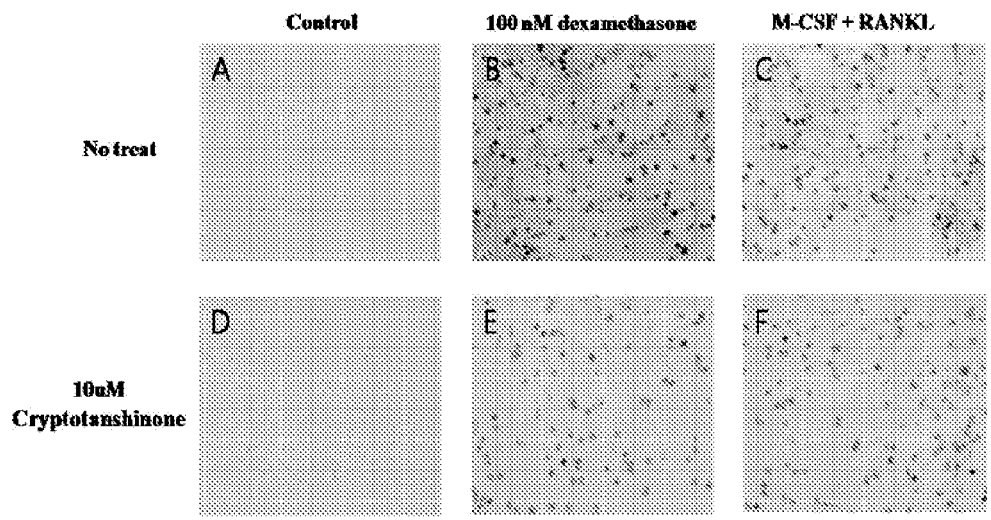
FIG. 3 shows TRAP assay results for confirming inhibition of differentiation of adipose tissue-derived stem cells into osteoclasts by the treatment of cryptotanshinone.

As a result, as shown in FIG. 3, in the medium treated with 100 nM dexamethasone and the osteoclast differentiation medium, after 7 days, osteoclast differentiation was observed, and when 10 μM cryptotanshinone was treated to each medium, the differentiated osteoclasts was decreased, and thus inhibition of osteoclast differentiation could be confirmed.

In addition, to identify a protein expressed in the induction of osteoclast differentiation, Western blot was performed.

Cells were dispensed in a 60 mm culture plate at $3 \times 10^6$ cells/well, and then an osteoclast differentiation medium or a medium prepared by adding 10 μM cryptotanshinone to the osteoclast differentiation medium was treated to incubate the cells for 7 days. The cells were washed with PBS three times, treated with a RIPA-B buffer (0.5% Nonidet P-40, 20 mM Tris, pH 8.0, 50 mM sodium chloride, 50 mM Sodium fluoride, 100 Sodium orthovanadate, 1 mM DTT, and 50/ml phenylmethanesulphonyl fluoride), remained for 1 hour at 4° C., and centrifuged at 4° C. at 2,000 rpm, thereby obtaining a protein. The obtained protein was transferred to a nitrocellulose membrane using a protein electrophoresis apparatus and transfer equipment by a conventional method, blocked with 5% skim milk (phosphate-buffered saline containing 5% skim milk and 0.05% Tween 20), treated with primary antibodies such as RANKL (Millipore; Concord Road, Billerica, Mass.), RANK (Millipore), OPG (Millipore) and GAPDH (Millipore) and a HRP-attached secondary antibody (Millipore), treated with an ECL solution (Amersham, Arlington, Heights, Ill.), and developed to an X-Ray film (Fuji film, Nishiazabu, Minato-ku, Tokyo, Japan).

Figure 4:
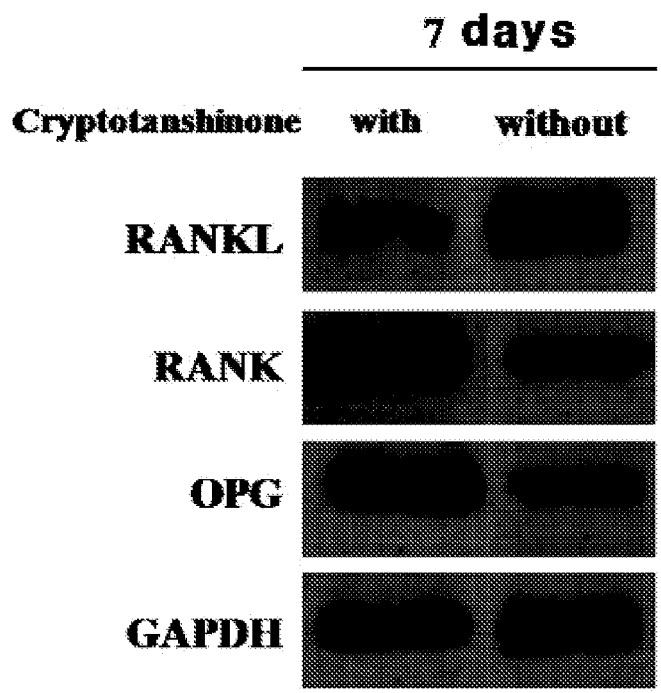
FIG. 4 shows Western blot results for confirming expression of osteoclast differentiation and inhibition-associated proteins to confirm inhibition of differentiation of adipose tissue-derived stem cells into osteoclasts by the treatment of cryptotanshinone.

As a result, as shown in FIG. 4, in the medium prepared by treating cryptotanshinone to the osteoclast differentiation medium, at the $7^{th}$ day, expression of RANKL inducing osteoclast differentiation was inhibited, but expression of OPG known as an osteoclast differentiation inhibitory factor was increased.

What is claimed is:

1. A method for stimulating differentiation of mesenchymal stem cells (MSCs) into osteoblasts in patients having osteoporosis, bone fracture or bone defects, or requiring bone graft, comprising administration to said patients a composition consisting of purified cryptotanshinone, MSCs, and a carrier.

2. The method of claim 1, wherein the cryptotanshinone is included at a concentration of 1 to 50 µM.

3. The method of claim 1, wherein the MSCs are obtained from tissue, bone marrow, cord blood, blood, or body fluid.

4. The method of claim 3, wherein the tissue is an adipose tissue.

5. The method of claim 1, wherein the cryptotanshinone is included at a concentration of 1 to 100 µM.

6. The method of claim 1, wherein an effective amount of the MSCs is $1 \times 10^4$ to $1 \times 10^6$ cells/kg.

* * * * *